United States Patent [19]

Pokrowsky et al.

[11] Patent Number: 5,502,567
[45] Date of Patent: Mar. 26, 1996

[54] MICROPOLARIMETER, MICROSENSOR SYSTEM AND METHOD OF CHARACTERIZING THIN FILMS

[75] Inventors: Peter Pokrowsky, Mainz; Eckehard Kiefer, Grafenau; Michael Abraham, Mainz; Bernd Stenkamp, Mainz; Wolfgang Ehrfeld, Mainz; Thomas Zetterer, Schwabenheim, all of Germany

[73] Assignee: International Business Machines Corporation, Armonk, N.Y.

[21] Appl. No.: 268,149

[22] Filed: Jun. 28, 1994

[30] Foreign Application Priority Data

Jun. 28, 1993 [EP] European Pat. Off. .............. 93110277

[51] Int. Cl.⁶ ........................................ G01J 4/00
[52] U.S. Cl. ............................... 356/367; 356/369
[58] Field of Search ........................... 356/364–370, 356/381, 382, 33–35; 250/225; 359/489, 501, 496

[56] References Cited

U.S. PATENT DOCUMENTS

| | | | |
|---|---|---|---|
| 3,759,618 | 9/1973 | Rogers et al. | 356/364 |
| 3,880,524 | 4/1975 | Dill et al. | 356/369 |
| 4,158,506 | 6/1979 | Collett | 356/365 |
| 4,286,843 | 9/1981 | Reytblatt | 356/33 |
| 4,585,348 | 4/1986 | Chastang et al. | 356/369 |
| 4,904,085 | 2/1990 | Spillman, Jr. et al. | 356/366 |
| 4,906,844 | 3/1990 | Hall | 356/369 |
| 4,944,579 | 7/1990 | Egan | 359/489 |
| 5,131,752 | 7/1992 | Yu et al. | 356/369 |
| 5,329,357 | 7/1994 | Bernoux et al. | 356/369 |
| 5,357,342 | 10/1994 | Decker et al. | 356/364 |

FOREIGN PATENT DOCUMENTS

| | | | |
|---|---|---|---|
| 0228721 | 10/1986 | European Pat. Off. | G01D 5/26 |
| 1951920 | 4/1971 | Germany | G01J 1/42 |
| 0456897 | 12/1990 | Germany | G01N 23/223 |
| 6229909 | 8/1994 | Japan | 356/64 |

OTHER PUBLICATIONS

N. P. Edwards et al., "Automated Ellipsometer", IBM Technical Disclosure Bulletin, vol. 18, No. 6, Nov. 1975, p. 2031.
F. H. Dill et al., "Ellipsometry with Pulsed Tunable Laser Sources", IBM Technical Disclosure Bulletin, vol. 19, No. 4, Sep. 1976, pp. 1487–1489.
R. M. A. Azzam et al., "Ellipsometry and Polarized Light", 1988, North Holland, Amsterdam, pp. x–xvii.

*Primary Examiner*—Hoa Q. Pham
*Attorney, Agent, or Firm*—Paik Saber

[57] ABSTRACT

A micropolarimeter comprises an analyzer (1) and a detector (3), which is typically a photodetector array. The detector has a circular configuration of a number N of sectors. Analyzer (1) and detector (3) form a unit with the analyzer assigning different polarization values to the sectors. Analyzer and the detector contain no moving parts. Three different embodiments are proposed for the analyzer: a glass cone, covered with a polarizing thin film stack, a metal grid polarizing array, and an array of polarizing waveguides. The micropolarimeter (14) is used preferably in a microellipsometer system which can serve as a tool for film diagnostics, especially optical characterization of thin films.

24 Claims, 4 Drawing Sheets

MICROPOLARIMETER, MICROSENSOR SYSTEM AND METHOD OF CHARACTERIZING THIN FILMS

BACKGROUND OF THE INVENTION

1. Field of the Invention

This invention relates to microsensor systems and to a micropolarimeter in which the micropolarimeter is designed to measure polarization states of light beams. The micropolarimeter is the central component in the following applications:

Ellipsometry for thin film diagnostics

Laser beam diagnostics

Diagnostics for polarization depending properties in optical fibers

Analysis of optically active materials.

2. Description of the Background Art

A well established method for characterizing surfaces and thin films is ellipsometry. A typical ellipsometer uses discrete polarization optical components in various combinations to determine the polarization state of light in terms of measured Stokes parameters. A detailed description is to be found in R. M. A. Azzam, N. M. Bashara, "Ellipsometry and Polarized Light", 1988, North Holland, Amsterdam.

Ellipsometry working principle is based on utilizing the variation in the intensity of the light detected as a function of the polarization ellipse parameters. Typically the polarizer is fixed and the analyzer is synchronously rotated about the light beam axis at a constant angular velocity, which is shown in various publications like IBM Technical Disclosure Bulletin 18 (1975) 2031.

The detector signal will exhibit periodic variations and is Fourier analyzed. Using the Fourier coefficients together with the known incident angle and the polarizer setting the ellipsometric angles are then derived.

For instrument operation precise mechanical motion of components is required limiting the response time of the instrument and complicating its design.

Instead of rotating components some polarimeters use modulation techniques modulating the phase and/or the azimuth of the beam. The analysis of the data obtained is, however, more complicated and expensive lock-in amplifiers and modulators are needed.

U.S. Pat. No. 4,585,348 discloses an ellipsometer having no moving parts and a minimum number of optical components. This instrument consists of a static photometric polarimeter and measures statically only the reflected intensities whose polarization lie, respectively, parallel and perpendicular to the plane defined by the incident and reflected beams. However, this instrument determines only the quotient of the two polarization states which is not sufficient to determine stokes parameters. For a complete determination of the Stokes parameters a second measurement is necessary.

In another kind of polarimetric systems moving or rotating elements are avoided by using multiple detector systems. IBM Technical Disclosure Bulletin 19 (1976) 1487 shows an arrangement using four beam splitters and four detectors which allows complete determination of the polarization state of light reflected from a sample directly in terms of measured Stokes parameters. The adjustment of the four independent beams, however, is very complicated and excludes the construction of a compact, small and fully-enclosed measuring apparatus.

U.S. Pat. No. 4,158,506 discloses a realtime polarimeter with pulse mode. A broadened beam enters six photodetectors with four of the polarizers being tilted in steps of $\pi/4$ and two of them form an angle of $\pi/2$ being arranged behind a $\lambda/4$ plate. By electronically adding and subtracting all the four Stokes parameters may be determined. However, due to the dimensions of conventional discrete polarizers the beam has to be strongly broadened which renders the characterization of small areas on a sample impossible without using additional optical elements.

Systems with multiple detectors have the problem of having only limited number of independent channels. Therefore noise reduction by carrying out further independent measurements similar to those in arrangements with rotating elements is not possible. The measuring accuracy thus remains far below the standard accuracy of conventional polarimeters and ellipsometers with rotating elements. Adding additional channels seems to be possible in principle, but unreasonably increases the technical effort and the costs.

It is the object of the present invention to provide a miniaturized measuring tool and a measuring concept which overcome the disadvantages of the prior art concepts and allow the use in on-line process control. This object and further positive effects are achieved by the invention as claimed.

SUMMARY OF THE INVENTION

The micropolarimeter of the present invention 1 comprises a unit of an analyzer and a detector having a circular configuration where the circular configuration is divided into a number N of sectors. The analyzer assigns different polarization values to the sectors.

The micropolarimeter is especially used as a detector in a microsensor system or in an arrangement of microsensor systems preferably for the following applications:

For the control of the polarization properties of continuous wave (cw) or pulsed lasers the beam is directed onto the polarimeter, which delivers real time data. The main advantage of this measurement technique is the ability to determine the polarization state of each laser pulse separately.

For the measurement of polarization dependent losses of optical fibers or integrated optical components like waveguides, light of defined polarization is coupled into the fiber or waveguide to be inspected. The micropolarimeter is used to analyze the polarization state at the output of the devices.

The change of polarization can be used for the concentration determination of optically active components in solution. The measurement is done in transmission using polarized light. The change of the polarization state is detected in real time by the micropolarimeter. In this configuration reaction kinetics can be observed.

In an ellipsometric arrangement for thin film diagnostics the micropolarimeter replaces the rotating analyzer.

By substituting a fixed miniaturized detector for a continuously rotating single polarizing element this invention eliminates any mechanical movement thus increasing the measuring accuracy and reducing the response time of the micropolarimeter drastically.

The micropolarimeter allows the easy production of a low cost, miniaturized, and compact sensor system which may be used for various applications and especially for on-line process control.

BRIEF DESCRIPTION OF THE DRAWINGS

Ways of carrying out the invention are described in detail below with reference to drawings showing only specific embodiments in which.

BEST MODE FOR CARRYING OUT THE INVENTION

Figure 1:
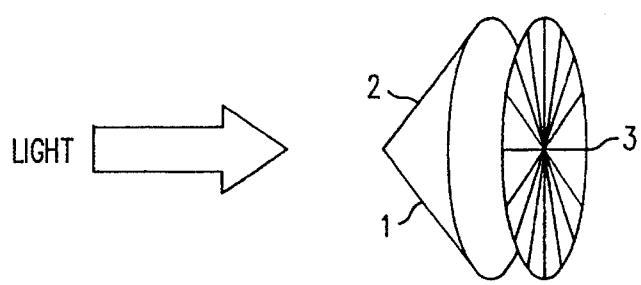
FIG. 1 is a preferred embodiment of the micropolarimeter which comprises a cone analyzer, polarizer coating, and a detector.

FIG. 1 shows a commercially available cone 1 of transparent material, preferably glass, which is covered on its convex surface with a polarizer coating 2 which comprises a multilayer system of transparent thin film layers. The polished cone has a cone diameter that allows a bundle of light being caught as a whole. A typical value of the cone diameter being approximately 1 mm. The dimension of the angle of opening allows, with light entering the cone parallel to the cone axis, for the polarizing properties of the polarizer coating 2 to take effect and to assign different polarization values to the detector 3 which forms a unit with the cone 1. Generally the angle of opening depends on the parameters of the multilayer system.

In a preferred embodiment the cone is made of fused silica with a refractive index of 1.46, an angle at the base of 40 to 60 degrees, a height of 2 mm and an outer diameter of 3.35 mm.

Figure 2:
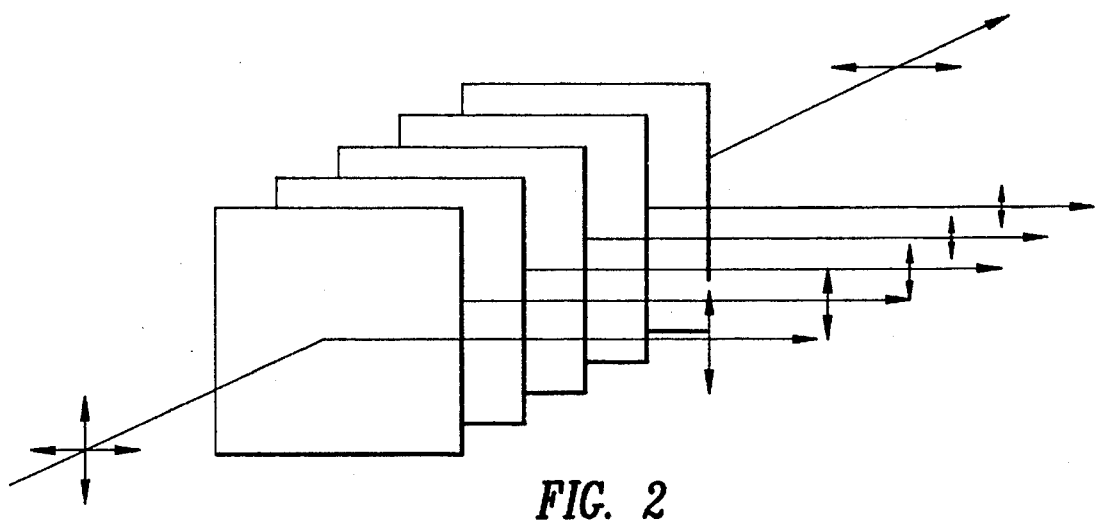
FIG. 2 shows a pile of plate polarizers.

The polarizer coating 2 comprises a multilayer system of transparent thin film layers. The basic principle of the cone polarizer may be understood from FIG. 2 showing a pile of plate polarizers. The light is polarized by transmission through a pile of plates inclined to the incident radiation at Brewster's angle. This is well known in the literature under the topic "Pile of Plate Polarizer" e.g., A. Elliott et al., J. Opt. Soc. Am. 38, 212, 1948.

The pile of plate polarizers can be realized by a system of thin film polarizers. In order to achieve a high degree of polarization, bigger than 10.000:1, it is necessary to have a great difference in the index of refraction n for the components of the film system on the convex surface of the cone 1, that means that the film system alternately shows layers with high and low refractive index.

Suitable low refractive index materials are magnesiumfluoride or siliconoxide and suitable high refractive index materials are titaniumoxide or zirconiumoxide.

The coating of the convex surface may be carried out by conventional coating methods like sputtering or evaporation.

In a preferred embodiment $TiO_2$ with a refractive index n=2.46 and $MgF_2$ with n=1.38 have been chosen. These materials may be evaporated in the same chamber while monitoring the optical thickness.

Figure 9:
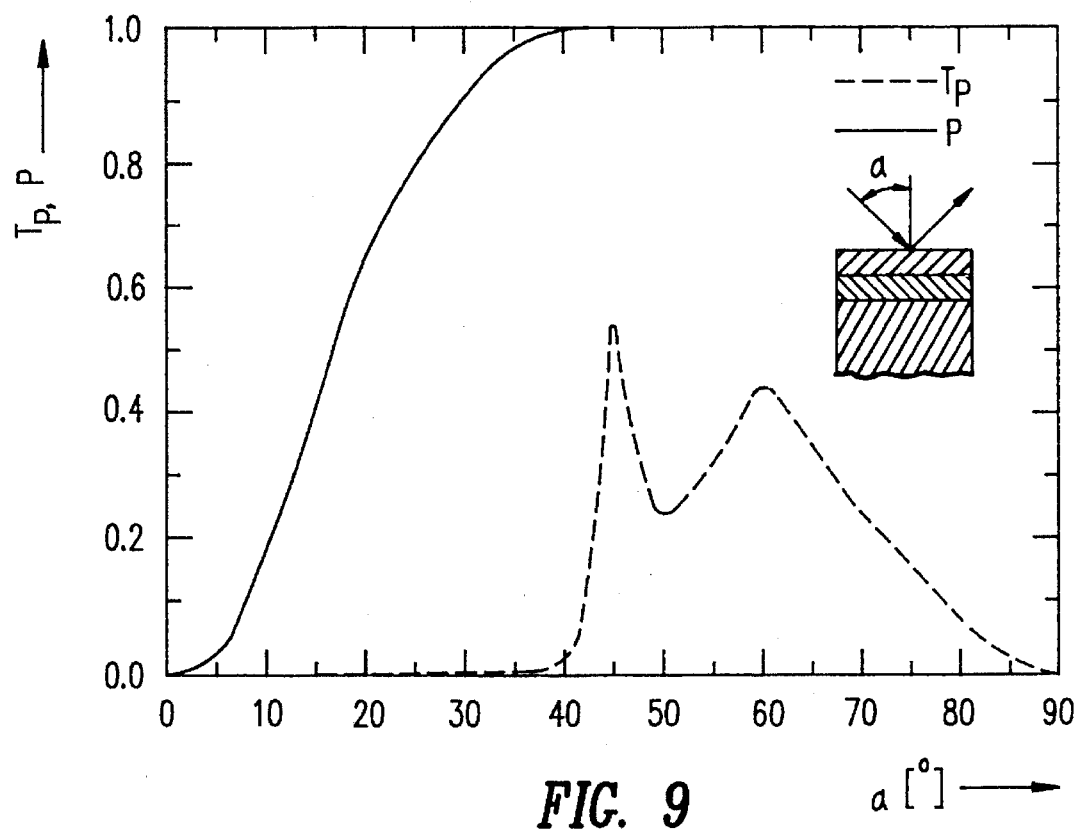
FIG. 9 is a representation of the measured transmission and the degree of polarization of the multilayer system of thin films on the cone.

The optical response of a similar system with 20 layers is to be seen in FIG. 9 showing the measured transmission Tp and the degree of polarization P of the multilayer system of thin films on the cone. The thickness of the $TiO_2$ layers is 60.5 nm, the thickness of the $MgF_2$ layers is 116.2 nm. This system leads to a degree of polarization greater than 10.000:1. Further optimization concerning the design of the film system is possible.

With its basal surface the coated cone 1 is adjusted and mounted onto a detector 3 with a circular configuration having the same diameter. The detector is divided into a number N of sensitive sectors of the same size. The cone 1 assigns different polarization values to the sectors. The cone 1 with the polarizer coating 2 and the mounted detector 3 together form the micropolarimeter.

The detector may be produced by known state of the art technologies like silicon planar technology. The fixing may be done by bonding or gluing with a transparent adhesive. The refractive index of the adhesive and the cone should have corresponding values to avoid interference between the surfaces of the cone 1 and the detector 3.

Figure 3:
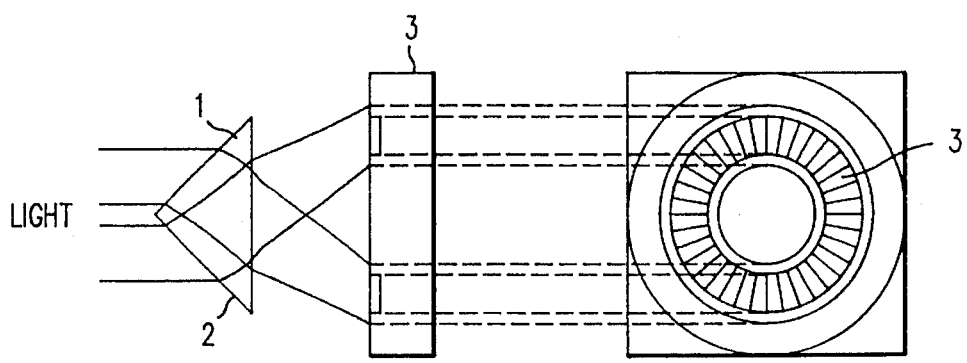
FIG. 3 is a cross section showing the principle of the micropolarimeter and the relative arrangement of the cone and detector.

The principle of the micropolarimeter and the relative arrangement of cone and detector are shown in FIG. 3. The light to be investigated enters the cone parallel to the cone axis. In accordance to the spatial position and the orientation of the polarization ellipse different amounts of light pass through the cone onto the sensitive N sectors of the detector. In the case of an even number of sensitive areas always one sector of each pair of sectors of the detector facing each other is redundant since both sectors receives the same polarization value and will integrate the same part of the polarization ellipse. Therefore the number of sectors must be at least six to allow the determination of the elliptic parameters. To increase the detection accuracy a higher number of sectors is necessary. The number of sectors is however limited by the ratio of the sensitive sector area to the width of the bars between the sectors. Each sector has to be individually readable.

The diameter of the input area of the micropolarimeter is typically smaller than the beam diameter of a light generating means, like a laser, by about 0.5 mm to 1.5 mm. This allows the parallel reading of the single sectors of the detector and the further treatment of the measured data with a computer.

In a preferred embodiment the detector is a photodetector array with 16 sectors of identical area in a complete circle. In another embodiment the detector has 64 sensitive sectors.

The quantity measured is the power $P_2$ detected by a sector element corresponding to the surface of a single detector surface. It can be calculated in the following way:

The N signals are used for the calculation of the ellipsometric parameters of the incoming light. Usually the detector contains N sensitive areas S (sensitive) separated by N nonsensitive areas. S gives the angular width and C the angular position of a given sector.

The ellipsometric parameters $\Delta$ and $\Psi$ can be calculated from the measured data $P_i$ from the following relations:

$$\tan(\Psi) = \sqrt{\frac{m_0 \frac{\sin(S)}{S} + m_1}{m_0 \frac{\sin(S)}{S} - m_1}}$$

$$\cos(\Delta) = \frac{m_2}{\sqrt{m_o^2 \frac{\sin^2(S)}{S^2} + m_1^2}}$$

The $m_i$ can be obtained from the measurement of the intensity per element $P_i$:

$$m_0 = \frac{1}{N} \sum_{i=1}^{n} P_i$$

$$m_1 = \frac{2}{N} \sum_{i=1}^{n} P_i \cdot \cos(2C_i)$$

$$m_2 = \frac{2}{N} \sum_{i=1}^{n} P_i \cdot \sin(2C_i)$$

In the case of the detector 3 with its circular configuration having an even number of sensitive areas, one area of each pair of areas which are facing each other is redundant since they detect exactly the same polarization value assigned by the cone 1. Thus, symmetry in the signals is assured when light incidents exactly in the optical axis of the cone.

This symmetry of signals has the advantage that it may be used in a very easy way to adjust the micropolarimeter without further means for adjusting. Thus, the redundancy of the sectors does not only increase the measuring accuracy but also simplifies the adjusting of the micropolarimeter significantly.

The adjustment can be done automatically by means of e.g., stepping motors or piezoelectric actuators until the symmetry of the signals on opposite sectors is reached.

By substituting an array of miniaturized fixed polarizing sectors for a continuously rotating single polarizing element the response time of the micropolarimeter is reduced drastically. The fixed polarizing sectors being arranged in the center of the reflected beam analyze simultaneously the state of polarization instead of serially detecting it with a single rotating element. Each sector is connected to a single photodetector and by electronic readout the complete information about the polarization may be rapidly transmitted to a computer for further data reduction.

Any mechanical movement is avoided which is very favorable for a low cost and miniaturized sensor system.

Figure 4:
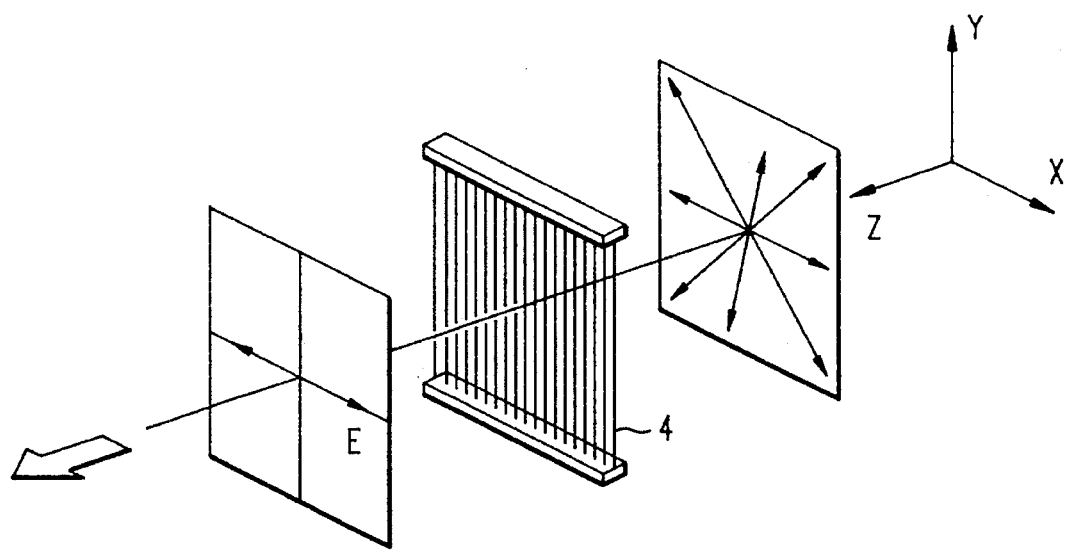
FIG. 4 shows the principle of the grid polarizer, another preferred embodiment of the micropolarimeter.

In another embodiment of the micropolarimeter instead of the transparent cone 1, the N sectors of the detector 3 contain metal grids 4. It is known that a grid of parallel metallic wires reflects radiation of one polarization while transmitting the other, provided the wavelength of radiation is about 10 times larger than the period of the grid. This basic principle of a grid polarizer is shown in FIG. 4, a survey of the theory is given in J. P. Auton, Applied Optics 6, 1023–1027, 1967.

These grids are preferably fabricated by directly writing with an electron beam pattern generator into the resist covered sectors of the detector or by other suitable microlithographical methods including e.g., lift-off techniques. Thus, the steps of adjusting cone 1 and detector 3 and of assembling these parts to a micropolarimeter are avoided. One possible way of manufacturing the grid detector comprises coating the active detector areas with a thin metal layer of Al or Cr, depositing electron beam resist, directly writing the grid structures into the resist, developing the resist and removing the unwanted metal stripes by etching.

Figure 5:
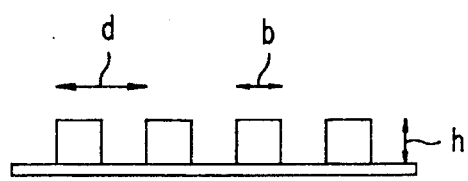
FIG. 5 gives an overview of the grid parameters.

The direction of the grids 4 varies from sector to sector in steps of $2\pi/N$. The grid parameters d, b and h are shown in FIG. 5. The metal grids should have a grid constant of approximately $\lambda/10$, that is approximately 50–100 nm for applications in the visible spectral region.

To get a high degree of polarization and high transmission, the ratio of $\lambda/d$ should be greater than five and the ratio of b/d should be about 0.5. The ratio of grid constant/$\lambda$ should be about 1:1.

Figure 10:
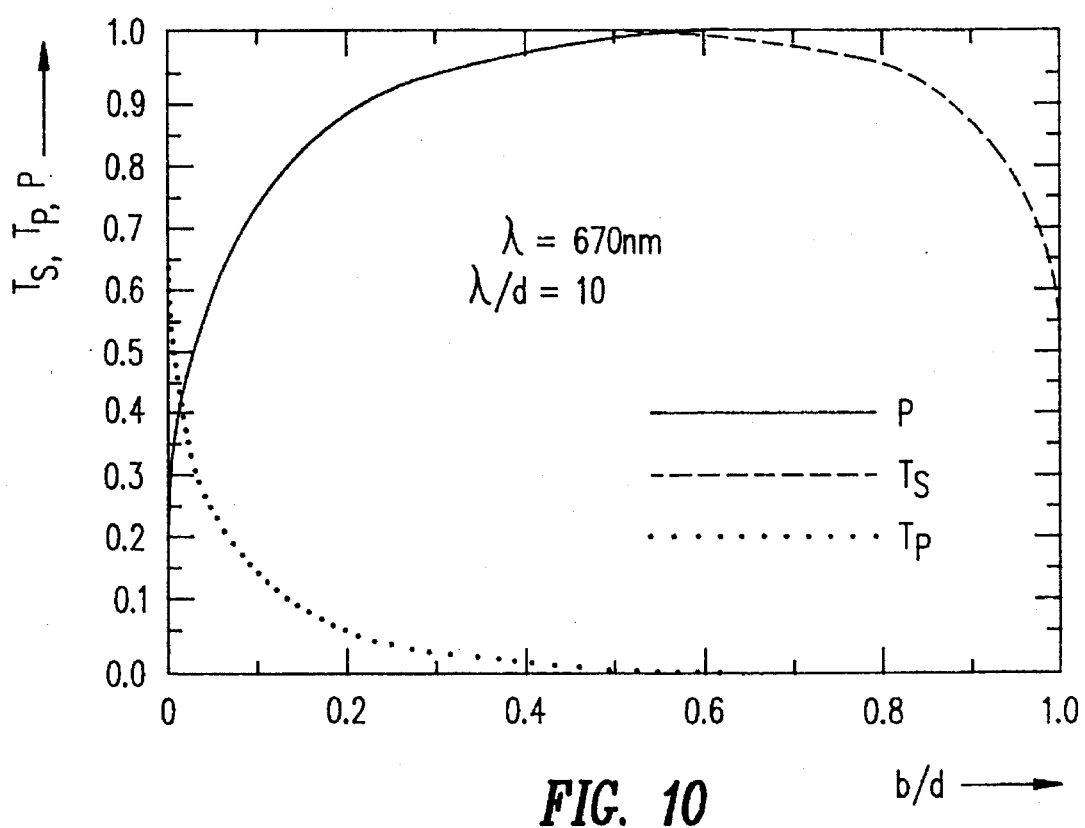
FIG. 10 is a simulation of the grid polarizer showing the calculated curves of the transmission and the degree of polarization.

In the past, this polarizer was always used in the infrared with wavelengths >10 μm. In a preferred embodiment for the visible spectral region with $\lambda$=670 nm the grids are made of Al or Cr with d=100 nm, b=50 nm and h=100 nm. FIG. 10 shows the calculated curves of the transmission T and the degree of polarization P for a grid polarizer.

Figure 6:
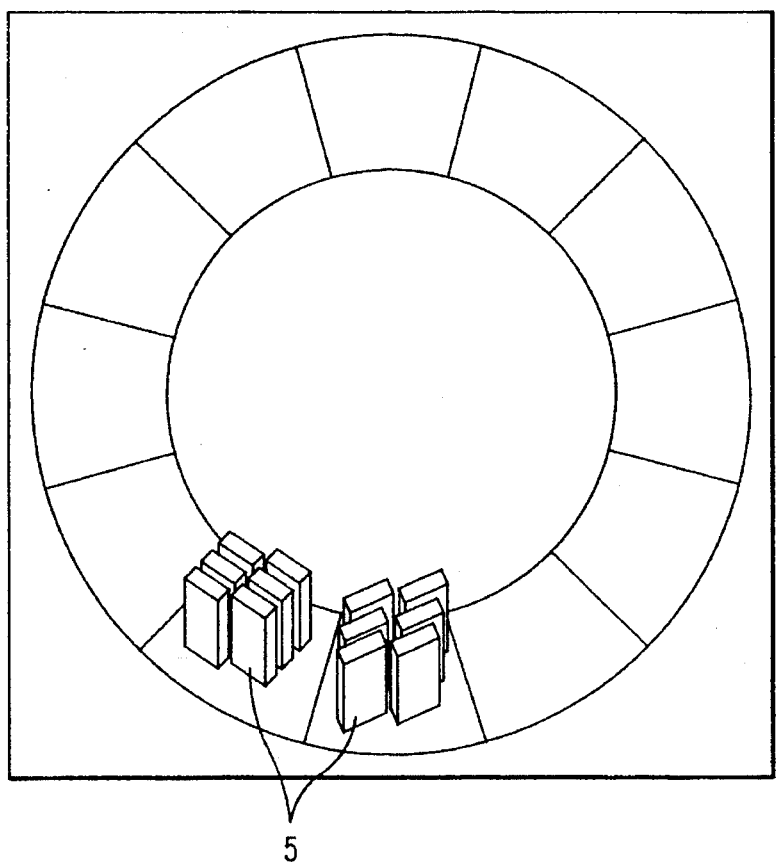
FIG. 6 shows some of the N sectors of the detector containing waveguides.

In a further embodiment instead of the cone 1, the N sectors of the detector 3 contain waveguides 5 as shown in FIG. 6. To increase signal intensity the detector surface is densely covered with waveguides positioned perpendicular to the surface of the detector with their axis lying substantially parallel to the optical axis of the micropolarimeter. The direction of the waveguides varies from sector to sector in steps of $2\pi/N$ similar to the varying direction of the metal grids in the embodiment of FIG. 4.

The function of the waveguides is based on the known principle of selective damping of transversal modes (TM) in a strip waveguide which is covered by a layer of a suitable metal due to excitation of surface plasmon as described, for example, in W. Karthe, R. Mueller "Integrierte Optik", Akademische Verlagsgesellschaft Geest und Portig, Leipzig, 1991.

The production of a waveguide array may be accomplished with the LIGA technique described in W. Ehrfeld, D. Münchmeyer, "Three-dimensional microfabrication using synchrotron radiation, Nucl. Instr. and Meth. A303, North Holland, pp. 523,1991. With this technique a metallic negative form of the waveguide array may be produced allowing to produce the basic structure of the detector by injection molding of a transparent polymer like polymethyl methacrylate (PMMA).

Then the sides of the waveguides are covered with a buffer layer of low refractive index by fluorination out of the gas or the liquid phase. Coating by evaporating the buffer layer here is not possible due to the tight distances between the waveguides. The next step is metallizing with a surface plasmon active material by evaporation and galvanization. After grinding the waveguide arrays produced in a batch mode process on the same wafer they are separated and glued to the detector.

Figure 7:
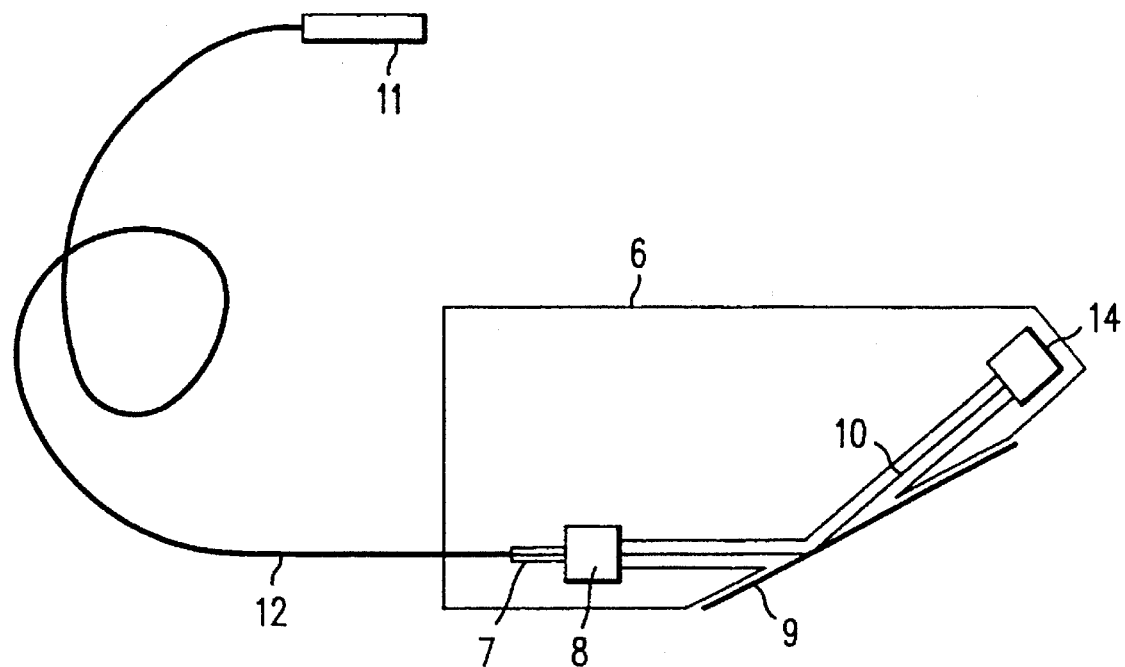
FIG. 7 gives an example of a possible set-up of a microsensor system.

FIG. 7 gives an example of a possible set-up of a microellipsometer system. The different parts of the system are assembled on a microoptical table 6. This table can be constructed by a computer numeric control (CNC) milling machine with an accuracy better than 0.02 mm. The microoptical table 6 positions the elements of the ellipsometer relative to each other with the needed accuracy thereby defining the beam path and especially the angle of incidence onto the sample 9. The desired incident angle is reached when the beam reflected from the sample 9 enters the detector 14 in its optical axis. Adjusting of the sample may be carried out manually or by use of suitable elements like stepper motors or piezoelements.

Typical dimensions of the microoptical table 6 are: length =50 mm, height=45 mm and width=10 mm.

The further elements of the microellipsometer are means 7 for collimating light like a gradient index (GRIN) lens, means 8 for polarizing light like a polarizing cube and means 14 for detecting the change of polarization after reflection of the light 10 from a sample 9. The means 14 for detecting is a micropolarimeter of one of the embodiments as described above.

A means 11 for generating light, preferably a laser or a powerful LED provides monochromatic, collimated and linear polarized light.

This light is guided to the microoptical table 6 by means 12 for guiding like a multimode or a monomode fiber. The fiber may be fixed to the microsensor by a special LIGA made fiber coupling insert.

This set-up of a microellipsometer system provides a very compact and small sensor which is suited for the use in the process line immediately after the respective layer formation steps. It has a large field of applications including thin film diagnostics and VLSI technology.

With this design the laser 11 is kept outside the microoptical table and the compact microsensor system.

One advantage of this feature is, that in case of laser failure it may simply be exchanged without distributing the microsensor itself and no cooling problems arise.

In another embodiment the means 11 for generating light may be integrated within the microsensor.

Figure 8:
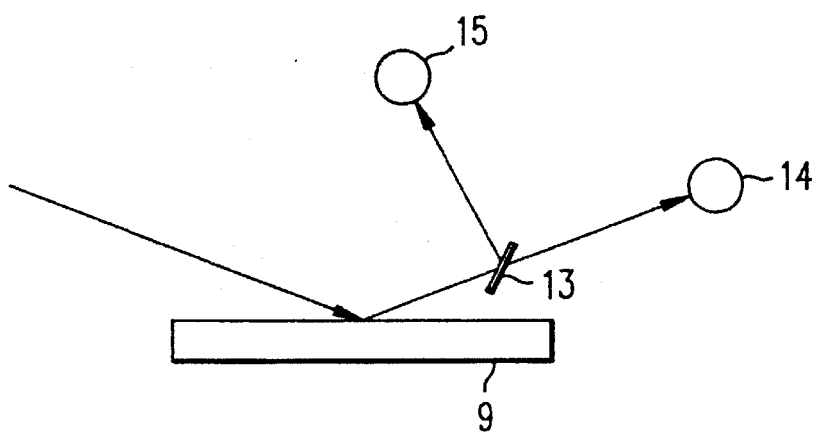
FIG. 8 shows another possible set-up of a microsensor system.

With the sensor described above it is possible to determine the orientation and the shape of the polarization ellipse. This is sufficient in most of the applications in thin film inspection. In order to obtain also the handedness of the elliptically polarized light, the set-up has to be modified as shown in FIG. 8.

A phase shifting beam splitter 13 or a beam splitter followed by a phase shifter is introduced into the beam path behind the sample 9 and deflects the light reflected from the sample via a $\pi/4$ plate or an equivalent phase-shifting element to a second means 15 for detecting. The second means 15 for detecting is preferably a micropolarimeter of one of the embodiments as described above. This set-up allows to double the number of independent measurements without considerably changing the size of the microsensor. In addition the absolute phase of the polarizing ellipse may be determined with this set-up which is not possible with measuring tools containing just rotating analyzer elements.

What we claim is:

1. A micropolarimeter, comprising:

a non-rotating detector having a circular configuration of N sectors; and a non-rotating analyzer for assigning polarization value to each of the sectors of said detector, said analyzer having an optical axis and further comprising a transparent cone having a convex surface and a base, with said non-rotating detector in direct contact with the base of said non-rotating analyzer.

2. A micropolarimeter as recited in claim 1, in which said transparent cone is selected from a group of material comprising of glass.

3. A micropolarimeter as recited in claim 1, in which said transparent cone is selected from a group of material comprising of fused silica.

4. A micropolarimeter as recited in claim 1, further comprising:

a polarizer coating having a multilayer system of transparent thin film layers covering the convex surface of said analyzer.

5. A micropolarimeter as recited in claim 4, in which said transparent thin film layers alternate in the value of their refractive index.

6. A micropolarimeter as recited in claim 4, in which said transparent thin film layers are selected from a group of materials comprising of titanumoxide.

7. A micropolarimeter as recited in claim 4, in which said transparent thin film layers are selected from a group of material comprising of zirconiumoxide.

8. A micropolarimeter as recited in claim 4, in which said transparent thin film layers are selected from a group of material comprising of magnesiumfluoride.

9. A micropolarimeter as recited in claim 4, in which said transparent thin film layers are selected from a group of material comprising of siliconoxide.

10. A micropolarimeter as recited in claim 1, in which one sector of each pair of opposite sectors is redundant.

11. A micropolarimeter as recited in claim 1, in which said non-rotating detector comprises an even number of sectors, thereby providing a means for adjusting said micropolarimeter with respect to its optical axis.

12. A micropolarimeter, comprising:

a non-rotating detector having a circular configuration of N sectors; and a non-rotating analyzer for assigning polarization value to each of the sectors of said detector, said analyzer having an optical axis and further comprising a plurality of metal grids, each metal grid having direct contact with one of the N sectors of said non-rotating detector, where the direction of said metal grids vary from sector to sector in steps of $2\pi/N$, said metal grids further having a grid constant of approximately $\lambda/10$.

13. A micropolarimeter, comprising:

a non-rotating detector having a circular configuration of N sectors; and a non-rotating analyzer for assigning polarization value to each of the sectors of said detector, said analyzer having an optical axis and further comprising a plurality of waveguides, each waveguide having direct contact with one of the N sectors of said non-rotating detector, where the direction of said waveguides vary in steps of $2\pi/N$ from sector to sector and with the axis of said waveguides lying substantially parallel to the optical axis of said micropolarimeter.

14. A microellipsometer system positioned on a microoptical table, comprising:

a light generating means;

means for collimating light from said light generating means;

a light polarizing means; and a first micropolarimeter for detecting the change of polarization after reflection of the polarized light from a sample, said first micropolarimeter comprising:

a non-rotating detector having a circular configuration of N sectors; and a non-rotating analyzer for assigning polarization value to each of the sectors of said non-rotating detector, said analyzer comprising a transparent cone having a convex surface and a base, with said non-rotating detector in direct contact with the base of said non-rotating analyzer.

15. A microellipsometer system as recited in claim 14 further comprising:

means for generating monochromatic light; and means for guiding said monochromatic light to said light collimating means.

16. A microellipsometer system as recited in claim 14, further comprising:
  a second micropolarimeter means for detecting the change of polarization after reflection of the polarized light from said sample;
  a phase shifting beam splitter means for deflecting the polarized light reflected from said sample, said phase shifting beam splitter means positioned between said sample and said second micropolarimeter means, said second micropolarimeter means comprising:
  a non-rotating detector having a circular configuration of N sectors; and
  a non-rotating analyzer for assigning polarization value to each of the sectors of said non-rotating detector.

17. A microellipsometer system as recited in claim 16, in which the non-rotating analyzer of said second micropolarimeter comprises a transparent cone having a convex surface and a base, with said second micropolarimeter non-rotating detector in direct contact with the base of said second micropolarimeter non-rotating analyzer.

18. A microellipsometer system as recited in claim 16, in which the non-rotating analyzer of said second micropolarimeter comprises a plurality of metal grids, each metal grid having direct contact with one of the N sectors of the non-rotating detector of said second micropolarimeter with the direction of said metal grids varying from sector to sector in steps of $2\pi/N$, said metal grids further having a grid constant of approximately $\lambda/10$.

19. A microellipsometer system as recited in claim 16, in which the non-rotating analyzer of said second micropolarimeter comprises a plurality of waveguides, each waveguide having direct contact with one of the N sectors of the non-rotating detector of said second micropolarimeter with the direction of said waveguides varying in steps of $2\pi/N$ from sector to sector and with the axis of said waveguides lying substantially parallel to the optical axis of said micropolarimeter.

20. A microellipsometer system positioned on a microoptical table, comprising:
  a light generating means;
  means for collimating light from said light generating means;
  a light polarizing means, and
  a first micropolarimeter for detecting the change of polarization after reflection of the polarized light from a sample, said first micropolarimeter comprising:
  a non-rotating detector having a circular configuration of N sectors; and
  a non-rotating analyzer for assigning polarization value to each of the sectors of said detector, said analyzer comprising a plurality of metal grids, each metal grid having direct contact with one of the N sectors of said non-rotating detector with the direction of said metal grids varying from sector to sector in steps of $2\pi/N$, said metal grids further having a grid constant of approximately $\lambda/10$.

21. A microellipsometer system positioned on a microoptical table, comprising:
  a light generating means;
  means for collimating light from said light generating means;
  a light polarizing means; and
  a first micropolarimeter for detecting the change of polarization after reflection of the polarized light from a sample, said first micropolarimeter comprising:
  a non-rotating detector having a circular configuration of N sectors; and
  a non-rotating analyzer for assigning polarization value to each of the sectors of said detector, said analyzer comprising a plurality of waveguides, each waveguide having direct contact with one of the N sectors of said non-rotating detector with the direction of said waveguides varying in steps of $2\pi/N$ from sector to sector and with the axis of said waveguides lying substantially parallel to the optical axis of said micropolarimeter.

22. A method of characterizing thin films using a microellipsometer system, comprising the steps of:
  placing a sample in said microellipsometer system;
  guiding polarized light to said sample;
  detecting the light reflected from said sample with a micropolarimeter, said micropolarimeter comprising:
  a non-rotating detector having a circular configuration of N sectors, and
  a non-rotating analyzer for assigning polarization value to each of the sectors of said detector, said non-rotating analyzer comprises a transparent cone having a convex surface and a base, with said non-rotating detector in direct contact with the base of said analyzer; and determining the polarization and the intensity of said reflected light.

23. A method of characterizing thin films using a microellipsometer system, comprising the steps of:
  placing a sample in said microellipsometer system;
  guiding polarized light to said sample;
  detecting the light reflected from said sample with a micropolarimeter, said micropolarimeter comprising:
  a non-rotating detector having a circular configuration of N sectors, and
  a non-rotating analyzer for assigning polarization value to each of the sectors of said detector, said non-rotating analyzer comprises a plurality of metal grids, each metal grid having direct contact with one of the N sectors of said non-rotating detector with the direction of said metal grids varying from sector to sector in steps of $2\pi/N$, said metal grids further having a grid constant of approximately $\lambda/10$; and determining the polarization and the intensity of said reflected light.

24. A method of characterizing thin films using a microellipsometer system, comprising the steps of:
  placing a sample in said microellipsometer system;
  guiding polarized light to said sample;
  detecting the light reflected from said sample with a micropolarimeter, said micropolarimeter comprising:
  a non-rotating detector having a circular configuration of N sectors, and
  a non-rotating analyzer for assigning polarization value to each of the sectors of said detector, said non-rotating analyzer comprises a plurality of waveguides, each waveguide having direct contact with one of the N sectors of said non-rotating detector with the direction of said waveguides varying in steps of $2\pi/N$ from sector to sector and with the axis of said waveguides lying substantially parallel to the optical axis of said micropolarimeter; and
  determining the polarization and the intensity of said reflected light.

* * * * *

UNITED STATES PATENT AND TRADEMARK OFFICE
CERTIFICATE OF CORRECTION

PATENT NO. : 5,502,567
DATED : March 26, 1996
INVENTOR(S) : Pokrowsky et al.

It is certified that error appears in the above-indentified patent and that said Letters Patent is hereby corrected as shown below:

Column 2, line 26, Delete "1".

Signed and Sealed this

Twentieth Day of August, 1996

Attest:

BRUCE LEHMAN

*Attesting Officer*     *Commissioner of Patents and Trademarks*

UNITED STATES PATENT AND TRADEMARK OFFICE
CERTIFICATE OF CORRECTION

PATENT NO. : 5,502,567
DATED : March 26, 1996
INVENTOR(S) : Pokrowsky et al.

It is certified that error appears in the above-indentified patent and that said Letters Patent is hereby corrected as shown below:

On the title page, item [73],

IN THE ASSIGNEE

After, International Business Machines Corporation, insert--
  IMM INSTITUT FUR MIKROTECHNIK GMBH, Mainz, Germany--.

Signed and Sealed this

Fourth Day of February, 1997

Attest:

BRUCE LEHMAN

*Attesting Officer*    *Commissioner of Patents and Trademarks*

UNITED STATES PATENT AND TRADEMARK OFFICE
CERTIFICATE OF CORRECTION

PATENT NO. : 5,502,567 Page 1 of 1
DATED : March 26, 1996
INVENTOR(S) : Pokrowsky et al.

It is certified that error appears in the above-identified patent and that said Letters Patent is hereby corrected as shown below:

<u>Title page,</u>
Item [73], Assignee, after "International Business Machines Corporation", insert
-- IMM Institut fur Mikrotechnik GmbH, Mainz, Germany --.

This certificate supersedes Certificate of Correction issued February 4, 1997.

Signed and Sealed this

Twenty-first Day of October, 2003

JAMES E. ROGAN
*Director of the United States Patent and Trademark Office*